United States Patent
Nakajima et al.

(10) Patent No.: US 8,548,598 B2
(45) Date of Patent: Oct. 1, 2013

(54) NERVE STIMULATION APPARATUS

(75) Inventors: Keiichiro Nakajima, Tokyo (JP); Hiroki Hibino, Tokyo (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 13/417,633

(22) Filed: Mar. 12, 2012

(65) Prior Publication Data
US 2013/0073006 A1    Mar. 21, 2013

(30) Foreign Application Priority Data
Sep. 15, 2011   (JP) ................... 2011-201949

(51) Int. Cl.
*A61N 1/00*     (2006.01)
(52) U.S. Cl.
USPC ......................................................... 607/62
(58) Field of Classification Search
USPC ...................... 607/62, 2, 9, 17, 25
See application file for complete search history.

(56) References Cited

U.S. PATENT DOCUMENTS

| | | | |
|---|---|---|---|
| 2007/0233192 A1* | 10/2007 | Craig | 607/2 |
| 2007/0250124 A1* | 10/2007 | Burnes et al. | 607/9 |
| 2008/0132966 A1* | 6/2008 | Levin et al. | 607/17 |
| 2012/0303084 A1* | 11/2012 | Kleckner et al. | 607/25 |

FOREIGN PATENT DOCUMENTS

WO    WO 2006/098996 A1    9/2006

* cited by examiner

*Primary Examiner* — Robert N Wieland
(74) *Attorney, Agent, or Firm* — Scully, Scott, Murphy & Presser, P.C.

(57) ABSTRACT

Provided is a nerve stimulation apparatus that is capable of performing effective nerve stimulation depending on a therapeutic purpose without adversely affecting a heart. Further provided is a nerve stimulation apparatus including: a stimulation-pulse output unit that outputs a stimulation pulse; a cardiac-event detector that detects a cardiac event; and a controller that controls the stimulation-signal output unit so as to output, during a cardiac refractory period, the nerve stimulation signal having an intensity that corresponds to the heart rate obtained on the basis of the cardiac event detected by the cardiac-event detector.

1 Claim, 12 Drawing Sheets

MODE: STIMULATION INTENSITY PER UNIT TIME IS PROPORTIONAL TO HEART RATE
EFFECT: TACHYCARDIA THERAPY

| HEART RATE [bpm] | PULSE VOLTAGE [V] | PULSE DURATION [ms] | NUMBER OF PULSES | PULSE PERIOD [ms] | NUMBER OF TIMES × PERIOD | STIMULATION INTENSITY PER UNIT TIME (RELATIVE VALUE) | RELATIVE INTENSITY (RELATIVE TO REFERENCE) | REGION |
|---|---|---|---|---|---|---|---|---|
| (1) | (2) | (3) | (4) | (5) | (4) × (5) | (1) × (2) × (3) × (4) | | |
| 30 | 5.0 | 2 | 5 | 20 | 100 | 1500 | 0.30 | |
| 35 | 5.0 | 2 | 5 | 20 | 100 | 1750 | 0.35 | |
| 40 | 5.0 | 2 | 5 | 20 | 100 | 2000 | 0.40 | |
| 45 | 5.0 | 2 | 5 | 20 | 100 | 2250 | 0.45 | |
| 50 | 5.0 | 2 | 5 | 20 | 100 | 2500 | 0.50 | |
| 55 | 5.0 | 2 | 5 | 20 | 100 | 2750 | 0.55 | |
| 60 | 5.0 | 2 | 5 | 20 | 100 | 3000 | 0.60 | |
| 65 | 5.0 | 2 | 5 | 20 | 100 | 3250 | 0.65 | |
| 70 | 5.0 | 2 | 5 | 20 | 100 | 3500 | 0.70 | |
| 75 | 5.0 | 2 | 5 | 20 | 100 | 3750 | 0.75 | |
| 80 | 5.0 | 2 | 5 | 20 | 100 | 4000 | 0.80 | |
| 85 | 5.0 | 2 | 5 | 20 | 100 | 4250 | 0.85 | |
| 90 | 5.0 | 2 | 5 | 20 | 100 | 4500 | 0.90 | |
| 95 | 5.0 | 2 | 5 | 20 | 100 | 4750 | 0.95 | |
| 100 | 5.0 | 2 | 5 | 20 | 100 | 5000 | 1.00 | |
| 105 | 5.0 | 2 | 5 | 20 | 100 | 5250 | 1.05 | |
| 110 | 5.0 | 2 | 5 | 20 | 100 | 5500 | 1.10 | |
| 115 | 5.0 | 2 | 5 | 20 | 100 | 5750 | 1.15 | |
| 120 | 5.0 | 2 | 5 | 20 | 100 | 6000 | 1.20 | |
| 125 | 5.0 | 2 | 5 | 20 | 100 | 6250 | 1.25 | |
| 130 | 5.0 | 2 | 5 | 20 | 100 | 6500 | 1.30 | |
| 135 | 5.0 | 2 | 5 | 20 | 100 | 6750 | 1.35 | |
| 140 | 5.0 | 2 | 5 | 20 | 100 | 7000 | 1.40 | |
| 145 | 5.0 | 2 | 5 | 20 | 100 | 7250 | 1.45 | |
| 150 | 5.0 | 2 | 5 | 20 | 100 | 7500 | 1.50 | |
| 155 | 5.0 | 2 | 5 | 20 | 100 | 7750 | 1.55 | |
| 160 | 5.0 | 2 | 5 | 20 | 100 | 8000 | 1.60 | |
| 165 | 5.0 | 2 | 5 | 20 | 100 | 8250 | 1.65 | |
| 170 | 5.0 | 2 | 5 | 20 | 100 | 8500 | 1.70 | |
| 175 | 5.0 | 2 | 5 | 20 | 100 | 8750 | 1.75 | |
| 180 | 5.0 | 2 | 5 | 20 | 100 | 9000 | 1.80 | |
| 185 | 5.0 | 2 | 5 | 20 | 100 | 9250 | 1.85 | |
| 190 | 5.0 | 2 | 5 | 20 | 100 | 9500 | 1.90 | |
| 195 | 5.0 | 2 | 5 | 20 | 100 | 9750 | 1.95 | |

MODE: RATE OF CHANGE OF STIMULATION INTENSITY PER UNIT TIME IS CHANGED IN ACCORDANCE WITH HEART RATE
EFFECT: TACHYCARDIA THERAPY

| HEART RATE [bpm] | PULSE VOLTAGE [V] | PULSE DURATION [ms] | NUMBER OF PULSES | PULSE PERIOD [ms] | NUMBER OF TIMES × PERIOD | STIMULATION INTENSITY PER UNIT TIME (RELATIVE VALUE) | RELATIVE INTENSITY (RELATIVE TO REFERENCE) | REGION |
|---|---|---|---|---|---|---|---|---|
| (1) | (2) | (3) | (4) | (5) | (4) × (5) | (1) × (2) × (3) × (4) | | |
| 30 | 3.0 | 1 | 1 | 20 | 20 | 90 | 0.02 | |
| 35 | 3.0 | 1 | 1 | 20 | 20 | 105 | 0.02 | C |
| 40 | 3.0 | 1 | 2 | 20 | 40 | 240 | 0.05 | |
| 45 | 3.0 | 1 | 3 | 20 | 60 | 405 | 0.08 | |
| 50 | 3.0 | 1 | 4 | 20 | 80 | 600 | 0.12 | |
| 55 | 3.0 | 1 | 5 | 20 | 100 | 825 | 0.17 | |
| 60 | 3.0 | 1.2 | 5 | 20 | 100 | 1080 | 0.22 | |
| 65 | 3.0 | 1.4 | 5 | 20 | 100 | 1365 | 0.27 | B |
| 70 | 3.0 | 1.6 | 5 | 20 | 100 | 1680 | 0.34 | |
| 75 | 3.0 | 1.8 | 5 | 20 | 100 | 2025 | 0.41 | |
| 80 | 3.0 | 2 | 5 | 20 | 100 | 2400 | 0.48 | |
| 85 | 3.5 | 2 | 5 | 20 | 100 | 2975 | 0.60 | |
| 90 | 4.0 | 2 | 5 | 20 | 100 | 3600 | 0.72 | |
| 95 | 4.5 | 2 | 5 | 20 | 100 | 4275 | 0.86 | |
| 100 | 5.0 | 2 | 5 | 20 | 100 | 5000 | 1.00 | A |
| 105 | 5.5 | 2 | 5 | 20 | 100 | 5775 | 1.16 | |
| 110 | 6.0 | 2 | 5 | 20 | 100 | 6600 | 1.32 | |
| 115 | 6.5 | 2 | 5 | 20 | 100 | 7475 | 1.50 | |
| 120 | 7.0 | 2 | 5 | 20 | 100 | 8400 | 1.68 | |
| 125 | 7.0 | 2.2 | 5 | 20 | 100 | 9625 | 1.93 | |
| 130 | 7.0 | 2.4 | 5 | 20 | 100 | 10920 | 2.18 | |
| 135 | 7.0 | 2.6 | 5 | 20 | 100 | 12285 | 2.46 | B |
| 140 | 7.0 | 2.8 | 5 | 20 | 100 | 13720 | 2.74 | |
| 145 | 7.0 | 3 | 5 | 20 | 100 | 15225 | 3.05 | |
| 150 | 7.0 | 3 | 6 | 20 | 120 | 18900 | 3.78 | C |
| 155 | 7.0 | 3 | 7 | 20 | 140 | 22785 | 4.56 | |
| 160 | 7.0 | 3 | 8 | 18 | 144 | 26880 | 5.38 | |
| 165 | 7.0 | 3 | 9 | 16 | 144 | 31185 | 6.24 | |
| 170 | 7.0 | 3 | 10 | 14 | 140 | 35700 | 7.14 | |
| 175 | 7.0 | 3 | 11 | 13 | 143 | 40425 | 8.09 | D |
| 180 | 7.0 | 3 | 12 | 12 | 144 | 45360 | 9.07 | |
| 185 | 7.0 | 3 | 13 | 11 | 143 | 50505 | 10.10 | |
| 190 | 7.0 | 3 | 14 | 10 | 140 | 55860 | 11.17 | |
| 195 | 7.0 | 3 | 15 | 9 | 135 | 61425 | 12.29 | |

MODE: STIMULATION INTENSITY PER UNIT TIME IS CONSTANT REGARDLESS OF HEART RATE
EFFECT: CARDIAC FAILURE THERAPY

| HEART RATE [bpm] | PULSE VOLTAGE [V] | PULSE DURATION [ms] | NUMBER OF PULSES | PULSE PERIOD [ms] | NUMBER OF TIMES × PERIOD | STIMULATION INTENSITY PER UNIT TIME (RELATIVE VALUE) | RELATIVE INTENSITY (RELATIVE TO REFERENCE) | REGION |
|---|---|---|---|---|---|---|---|---|
| (1) | (2) | (3) | (4) | (5) | (4) × (5) | (1) × (2) × (3) × (4) | | |
| 30 | 7.0 | 3 | 8 | 18 | 144 | 5040 | 1.01 | D |
| 35 | 7.0 | 3 | 7 | 20 | 140 | 5145 | 1.03 | C |
| 40 | 7.0 | 3 | 6 | 20 | 120 | 5040 | 1.01 | |
| 45 | 7.0 | 3 | 5 | 20 | 100 | 4725 | 0.95 | B |
| 50 | 7.0 | 2.8 | 5 | 20 | 100 | 4900 | 0.98 | |
| 55 | 7.0 | 2.6 | 5 | 20 | 100 | 5005 | 1.00 | |
| 60 | 7.0 | 2.4 | 5 | 20 | 100 | 5040 | 1.01 | |
| 65 | 7.0 | 2.2 | 5 | 20 | 100 | 5005 | 1.00 | |
| 70 | 7.0 | 2 | 5 | 20 | 100 | 4900 | 0.98 | A |
| 75 | 6.7 | 2 | 5 | 20 | 100 | 5000 | 1.00 | |
| 80 | 6.3 | 2 | 5 | 20 | 100 | 5000 | 1.00 | |
| 85 | 5.9 | 2 | 5 | 20 | 100 | 5000 | 1.00 | |
| 90 | 5.6 | 2 | 5 | 20 | 100 | 5000 | 1.00 | |
| 95 | 5.3 | 2 | 5 | 20 | 100 | 5000 | 1.00 | |
| 100 | 5.0 | 2 | 5 | 20 | 100 | 5000 | 1.00 | |
| 105 | 4.8 | 2 | 5 | 20 | 100 | 5000 | 1.00 | |
| 110 | 4.5 | 2 | 5 | 20 | 100 | 5000 | 1.00 | |
| 115 | 4.3 | 2 | 5 | 20 | 100 | 5000 | 1.00 | |
| 120 | 4.2 | 2 | 5 | 20 | 100 | 5000 | 1.00 | |
| 125 | 4.0 | 2 | 5 | 20 | 100 | 5000 | 1.00 | |
| 130 | 4.0 | 2 | 5 | 20 | 100 | 5200 | 1.04 | |
| 135 | 3.7 | 2 | 5 | 20 | 100 | 5000 | 1.00 | |
| 140 | 3.6 | 2 | 5 | 20 | 100 | 5000 | 1.00 | |
| 145 | 3.4 | 2 | 5 | 20 | 100 | 5000 | 1.00 | |
| 150 | 3.3 | 2 | 5 | 20 | 100 | 5000 | 1.00 | |
| 155 | 3.2 | 2 | 5 | 20 | 100 | 5000 | 1.00 | |
| 160 | 3.1 | 2 | 5 | 20 | 100 | 5000 | 1.00 | |
| 165 | 3.0 | 2 | 5 | 20 | 100 | 5000 | 1.00 | |
| 170 | 3.0 | 2 | 5 | 20 | 100 | 5100 | 1.02 | B |
| 175 | 3.0 | 1.8 | 5 | 20 | 100 | 4725 | 0.95 | |
| 180 | 3.0 | 1.8 | 5 | 20 | 100 | 4860 | 0.97 | |
| 185 | 3.0 | 1.8 | 5 | 20 | 100 | 4995 | 1.00 | |
| 190 | 3.0 | 1.8 | 5 | 20 | 100 | 5130 | 1.03 | |
| 195 | 3.0 | 1.6 | 5 | 20 | 100 | 4680 | 0.94 | |

MODE: STIMULATION INTENSITY PER UNIT TIME
      IS INVERSELY PROPORTIONAL TO HEART RATE
EFFECT: BRADYCARDIA THERAPY

| HEART RATE [bpm] | PULSE VOLTAGE [V] | PULSE DURATION [ms] | NUMBER OF PULSES | PULSE PERIOD [ms] | NUMBER OF TIMES × PERIOD | STIMULATION INTENSITY PER UNIT TIME (RELATIVE VALUE) | RELATIVE INTENSITY (RELATIVE TO REFERENCE) | REGION |
|---|---|---|---|---|---|---|---|---|
| (1) | (2) | (3) | (4) | (5) | (4) × (5) | (1) × (2) × (3) × (4) | | |
| 40 | 7.0 | 3 | 16 | 9 | 144 | 13440 | 4.48 | D |
| 41 | 7.0 | 3 | 15 | 9 | 135 | 12915 | 4.31 | |
| 42 | 7.0 | 3 | 14 | 10 | 140 | 12348 | 4.12 | |
| 43 | 7.0 | 3 | 13 | 11 | 143 | 11739 | 3.91 | |
| 44 | 7.0 | 3 | 12 | 12 | 144 | 11088 | 3.70 | |
| 45 | 7.0 | 3 | 11 | 13 | 143 | 10395 | 3.47 | |
| 46 | 7.0 | 3 | 10 | 14 | 140 | 9660 | 3.22 | |
| 47 | 7.0 | 3 | 9 | 16 | 144 | 8883 | 2.96 | |
| 48 | 7.0 | 3 | 8 | 18 | 144 | 8064 | 2.69 | |
| 49 | 7.0 | 3 | 7 | 20 | 140 | 7203 | 2.40 | C |
| 50 | 7.0 | 3 | 6 | 20 | 120 | 6300 | 2.10 | |
| 51 | 7.0 | 3 | 5 | 20 | 100 | 5355 | 1.79 | B |
| 52 | 7.0 | 2.8 | 5 | 20 | 100 | 5096 | 1.70 | |
| 53 | 7.0 | 2.6 | 5 | 20 | 100 | 4823 | 1.61 | |
| 54 | 7.0 | 2.4 | 5 | 20 | 100 | 4536 | 1.51 | |
| 55 | 7.0 | 2.2 | 5 | 20 | 100 | 4235 | 1.41 | |
| 56 | 7.0 | 2 | 5 | 20 | 100 | 3920 | 1.31 | A |
| 57 | 6.5 | 2 | 5 | 20 | 100 | 3705 | 1.24 | |
| 58 | 6.0 | 2 | 5 | 20 | 100 | 3480 | 1.16 | |
| 59 | 5.5 | 2 | 5 | 20 | 100 | 3245 | 1.08 | |
| 60 | 5.0 | 2 | 5 | 20 | 100 | 3000 | 1.00 | |
| 61 | 4.5 | 2 | 5 | 20 | 100 | 2745 | 0.92 | |
| 62 | 4.0 | 2 | 5 | 20 | 100 | 2480 | 0.83 | |
| 63 | 3.5 | 2 | 5 | 20 | 100 | 2205 | 0.74 | |
| 64 | 3.0 | 2 | 5 | 20 | 100 | 1920 | 0.64 | |
| 65 | 3.0 | 1.8 | 5 | 20 | 100 | 1755 | 0.59 | B |
| 66 | 3.0 | 1.6 | 5 | 20 | 100 | 1584 | 0.53 | |
| 67 | 3.0 | 1.4 | 5 | 20 | 100 | 1407 | 0.47 | |
| 68 | 3.0 | 1.2 | 5 | 20 | 100 | 1224 | 0.41 | |
| 69 | 3.0 | 1 | 5 | 20 | 100 | 1035 | 0.35 | |

FIG. 12

NERVE STIMULATION APPARATUS

CROSS-REFERENCE TO RELATED APPLICATIONS

This application is based on Japanese Patent Application No. 2011-201949, the contents of which are incorporated herein by reference.

BACKGROUND OF THE INVENTION

1. Field of the Invention

The present invention relates to a nerve stimulation apparatus.

2. Description of Related Art

Stimulation of the vagus nerve on a patient who has experienced cardiac infarction has conventionally known to be capable of suppressing cardiac remodeling (for example, see WO2006/098996). In addition, it has been proposed that stimulation of the vagus nerve over a long period of time on a patient experiencing cardiac failure can potentially prevent progress of the disease.

In the related art described above, in order to perform cardiac treatment on a patient, remodeling control therapy is performed by biventricular pacing, and anti-remodeling therapy is performed by nerve stimulation. In addition, by performing nerve stimulation in the cardiac refractory period, undesired stimulation of the heart due to leakage of nerve stimulation is prevented so that the heart is not adversely affected.

BRIEF SUMMARY OF THE INVENTION

The present invention provides a nerve stimulation apparatus that is capable of performing effective nerve stimulation depending on the therapeutic purpose while preventing the heart from being adversely affected.

The present invention employs following solution.

An aspect of according to the present invention is a nerve stimulation apparatus including: a stimulation-signal output unit that outputs a nerve stimulation signal; a cardiac-event detector that detects a cardiac event; and a controller that controls the stimulation-signal output unit so as to output, during a cardiac refractory period, the nerve stimulation signal having an intensity that corresponds to the heart rate obtained on the basis of the cardiac event detected by the cardiac-event detector.

DETAILED DESCRIPTION OF THE INVENTION

The nerve stimulation apparatus 1 according to an embodiment of the present invention will be described below, with reference to the drawings.

Figure 1:
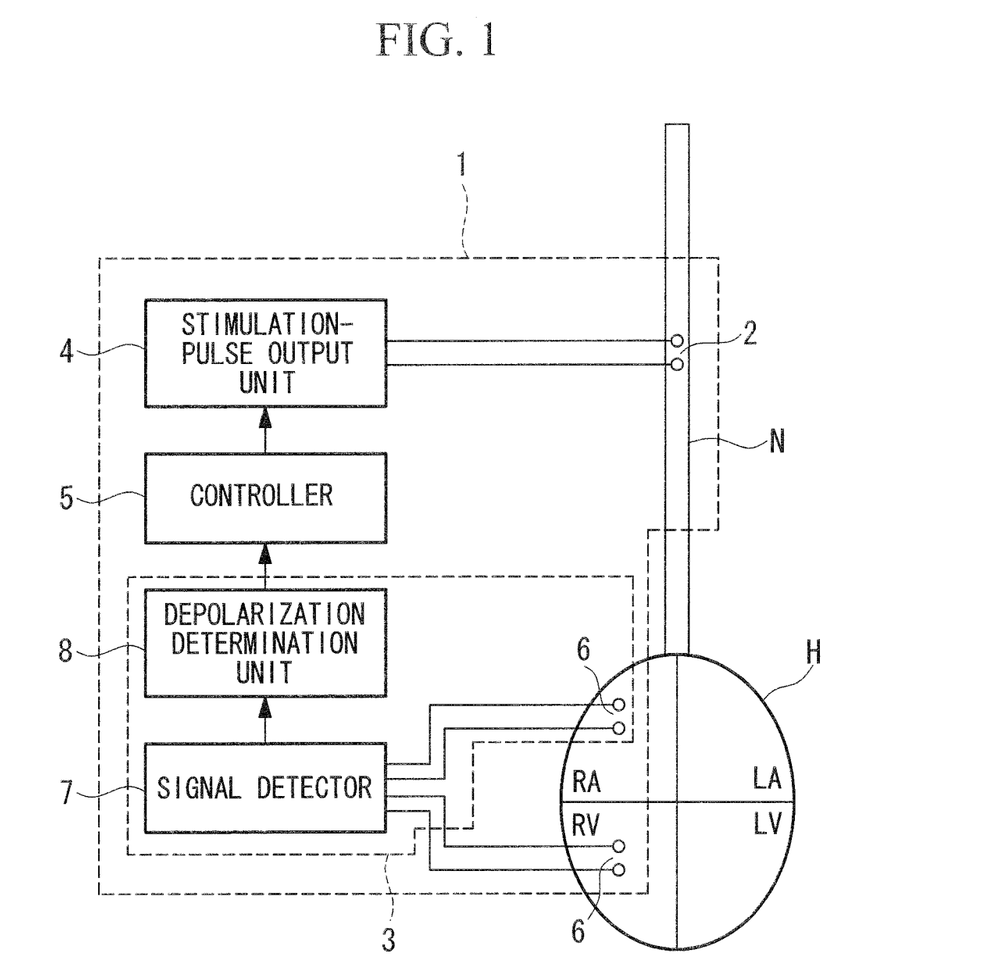
FIG. 1 is a diagram showing the overall configuration of a nerve stimulation apparatus according to an embodiment of the present invention.

As shown in FIG. 1, the nerve stimulation apparatus 1 according to this embodiment is provided with electrodes 2 attached to a nerve N in the vicinity of a heart H, such as the vagus nerve etc., a cardiac-event detector 3 that detects an event in the heart H (cardiac event), a stimulation-pulse output unit (stimulation-signal output unit) 4 that outputs a stimulation pulse (nerve stimulation signal) to the nerve N through the electrodes 2, and a controller 5 that controls the stimulation-pulse output unit 4 on the basis of the cardiac event detected by the cardiac-event detector 3.

The cardiac-event detector 3 is provided with two or more indwelling detection electrodes 6 that are in contact with parts of the heart H (for instance, in the example shown in FIG. 1, the right atrium RA and the right ventricle RV), a signal detector 7 that detects an electrocardiac signal though the two or more detection electrodes 6, and a depolarization determination unit 8 that determines that, when the signal detected with the signal detector 7 exceeds a predetermined threshold, the heart H is undergoing depolarization at that point. In the figure, reference sign LA is the left atrium, and reference sign LV is the left ventricle.

In the example shown in FIG. 1, the detection electrodes 6 are placed in the right atrium RA and the right ventricle RV; however, depolarization may be determined by using either an electrocardiac signal of the right atrium RA or an electrocardiac signal of the right ventricle RV, or both.

In addition, the locations where the detection electrodes 6 are placed are not limited to the right atrium RA and the right ventricle RV: for example, the left atrium LA and the left ventricle LV may be used.

The respective detection electrodes 6 consist of a cathode (tip electrode) and an anode (ring electrode), and the respective electrodes are connected to conductive wires. The conductive wires are coated with an insulator so as not to cause a short circuit between the cathode and the anode. These insulator-coated wires are further coated with an insulator after the two wires are bound together (in the figure, the insulating coating is omitted). The signal detector 7 detects an electric potential difference formed between the cathode and the anode of the respective detection electrodes 6 as an electrocardiac signal.

The stimulation-pulse output unit 4 generates a stimulation pulse train for electrically stimulating the nerve N and supplies the nerve N with the generated stimulation pulse train via the electrodes 2. Parameters that determine the intensity of the stimulation pulse train include pulse voltage, pulse duration, number of pulses, and pulse period (frequency). A group of these parameters is called a burst, and the number of pulses in one burst is called the number of pulses. In addition, the interval between the bursts is called a burst period.

The electrodes 2 also consist of a cathode (tip electrode) and an anode (ring electrode), and the respective electrodes are connected to conductive wires. The conductive wires are coated with an insulator so as not to cause a short circuit between the cathode and the anode. These insulator-coated wires are further coated with an insulator after the two wires are bound together (in the figure, the insulator coating is omitted). The stimulation-pulse output unit 4 outputs the stimulation pulse train, which is to be supplied to the nerve N, between the cathode and the anode of the electrodes 2.

When the depolarization determination unit 8 determines that depolarization of the heart H has occurred, it outputs to the controller 5 a signal indicating that the depolarization has occurred.

The controller 5 is provided with a timer (not shown). The controller 5 resets the timer and starts measuring the elapsed time every time the signal indicating the occurrence of depolarization is received from the depolarization determination unit 8.

A refractory period of the heart H of 150 ms, for example, is stored and held in the controller 5 as a predetermined value, and the period of 150 ms from the time at which the signal indicating the occurrence of depolarization is received from the depolarization determination unit 8 is determined as the refractory period. In addition, the controller 5 controls the stimulation-pulse output unit 4 so as to output, during cardiac refractory periods, stimulation pulses having an intensity that corresponds to the heart rate obtained on the basis of the cardiac event detected by the cardiac-event detector 3. The value of this refractory period is stored and held in the controller 5 by inputting to the controller 5, in advance, an actually measured value of the duration of the refractory period of a patient or a general value.

In particular, the controller 5 changes at least one of the pulse voltage, the pulse duration, the number of pulses, and the pulse period of the stimulation pulse output from the stimulation-pulse output unit 4 in accordance with the selected stimulation mode. The intensity of the stimulation pulse per burst can be defined by three parameters, i.e. the pulse voltage, the pulse duration, and the number of pulses, and in addition, a stimulation intensity per unit time can be defined by taking a parameter of the burst period into account. In this embodiment, the burst periods are matched with the depolarization intervals. Therefore, the controller 5 can change the intensity of the nerve stimulation signal output from the stimulation-pulse output unit 4 by changing at least one of the pulse voltage, the pulse duration, and the number of pulses.

The stimulation mode includes a proportional mode in which the stimulation pulse intensity is proportional to the heart rate, a variable rate-of-change-of-intensity mode in which the rate of change of the stimulation pulse intensity is changed according to the heart rate, a nonvariable mode in which the stimulation pulse intensity is maintained constant, and an inversely proportional mode in which the stimulation pulse intensity is inversely proportional to the heart rate. Details of these stimulation modes will be described later.

Figure 2:
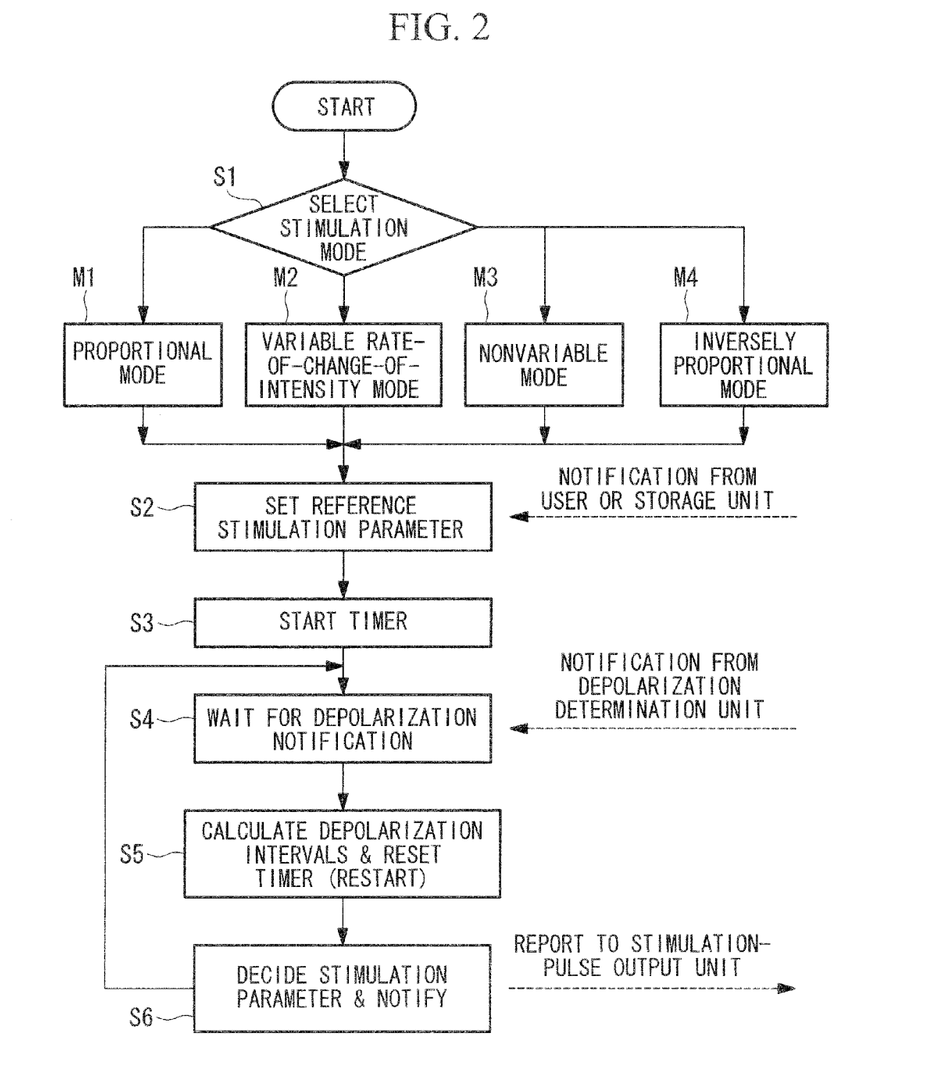
FIG. 2 is a flowchart showing a procedure for the nerve stimulation apparatus of FIG. 1.

A procedure for the nerve stimulation apparatus 1 according to this embodiment, having the configuration described above, will be described below according to the flowchart in FIG. 2.

In the nerve stimulation apparatus 1 according to this embodiment, selection of the aforementioned stimulation mode (the proportional mode M1, the variable rate-of-change-of-intensity mode M2, the nonvariable mode M3, and the inversely proportional mode M4) is performed (Step S1). At this time, the selection of the stimulation mode may be performed by pushing a switch (not shown) etc. provided on the nerve stimulation apparatus 1 or by being programmed by a user.

Next, reference stimulation parameters for the stimulation pulse intensity and the amounts of change of the parameters are set (Step S2). The setting may be performed by a user through an external program or by utilizing values preset in a memory (not shown) of the nerve stimulation apparatus 1.

Next, an electrocardiac signal formed across the detection electrodes 6 of the cardiac-event detector 3 that indwell in the heart H is detected with the signal detector 7, the occurrence of depolarization of the heart H is determined by the depolarization determination unit 8 when the detected electrocardiac signal exceeds a predetermined threshold, and a signal indicating so is sent to the controller 5.

As the signal indicating that the depolarization has occurred is sent to the controller 5, the controller 5 resets the timer to start the timer for measuring depolarization intervals (Step S3).

Thereafter, the controller 5 stands-by until it receives a depolarization notification from the depolarization determination unit 8 while keep measuring the elapsed time with the timer (Step S4).

The controller 5 calculates a depolarization interval every time it receives a depolarization notification from the depolarization determination unit 8 and resets the timer (restarts) (Step S5).

Thereafter, on the basis of the depolarization interval (the instantaneous heart rate) and the reference stimulation parameters, the controller 5 decides stimulation parameters and notifies the stimulation-pulse output unit 4 of the stimulation parameters (Step S6).

Unless a termination notification is received from a user or a program, the aforementioned Steps S4 to S6 are repeated.

Next, an operation example of the nerve stimulation apparatus 1 according to this embodiment will be described below with reference to the time charts of FIG. 3.

Figure 3:
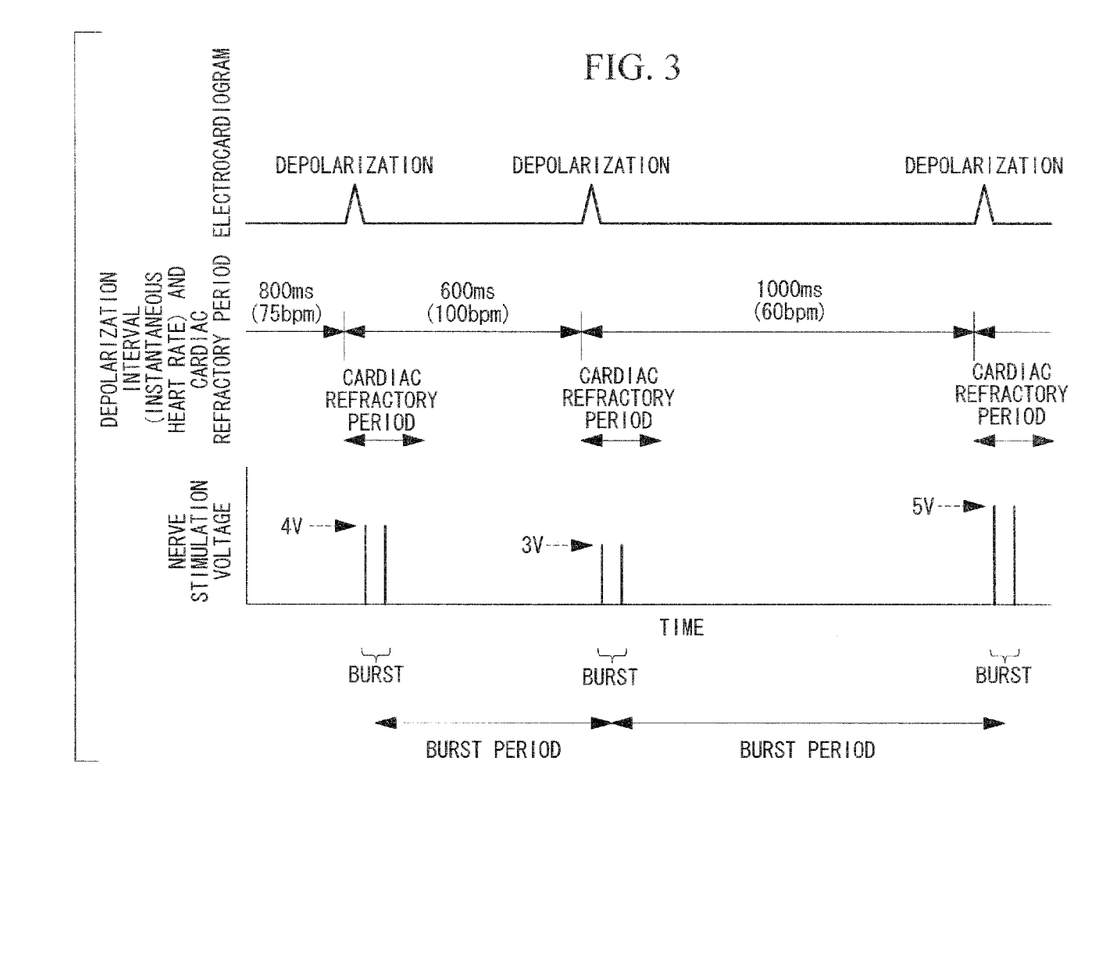
FIG. 3 is a time chart showing the relationship between an electrocardiac signal and a stimulation intensity of the nerve stimulation apparatus of FIG. 1.

In FIG. 3, the top section shows the electrical activity of the heart detected with the signal detector 7 and timings (parts indicated as "depolarization" in the figure) at which depolarizations are determined with the depolarization determination unit 8.

In FIG. 3, the middle section shows the depolarization intervals (800 ms, 600 ms, and 1000 ms) and duration of the cardiac refractory period measured by the controller 5 using the timer. In the figure, numerical values in parentheses (75 bpm, 100 bpm, and 60 bpm) indicate the instantaneous heart rate, and the cardiac refractory period is for example, 150 ms.

The bottom section in FIG. 3 shows a situation in which the stimulation-pulse output unit 4, which has been notified of the stimulation parameters from the controller 5, is outputting the stimulation pulses during the cardiac refractory periods. The vertical axis indicates the nerve stimulation voltage, in particular, voltages of the stimulation pulses, and the voltages are, for example, 4 V, 3 V, and 5 V.

The depolarization intervals and the heart rate will now be explained.

As shown in the following equation, the heart rate (unit: bpm) normally means the number of heartbeats (=the number of depolarizations) per minute; however, a depolarization interval converted to heart rate can also be called the heart rate (strictly, the instantaneous heart rate).

Heart Rate (Instantaneous Heart Rate)=60000 [ms]
÷Depolarization Interval [ms]

Figure 4:
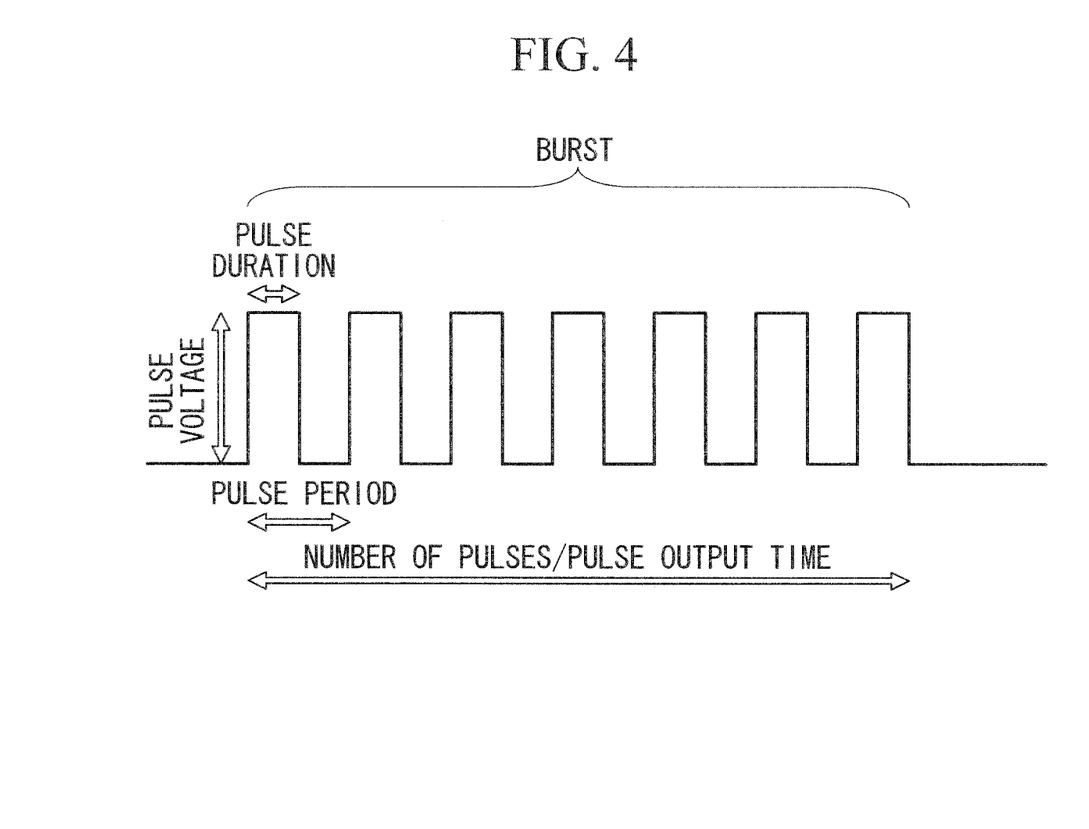
FIG. 4 is a diagram showing stimulation pulses output by the nerve stimulation apparatus of FIG. 1.

In addition, an example of the stimulation pulses is shown in FIG. 4.

The parameters notified to the stimulation-pulse output unit 4 from the controller 5 include the pulse voltage, the pulse duration, the pulse period, and the number of pulses. As mentioned above, the intensity of the stimulation pulse per burst can be defined by three parameters, i.e., the pulse voltage, the pulse duration, and the number of pulses. Each of the parameters may be changed independently to change the intensity, or two or more parameters may be changed in combination to change the intensity.

As described above, according to the nerve stimulation apparatus 1 of this embodiment, the cardiac-event detector 3 detects the cardiac event, and the heart rate is obtained on the basis of the cardiac event. The controller 5 then controls the stimulation-pulse output unit 4 so as to output, during the cardiac refractory period, a stimulation pulse having an intensity corresponding to the heart rate.

By performing nerve stimulation during the cardiac refractory period in such a manner, it is possible to prevent undesired stimulation of the heart due to leakage of nerve stimulation and to prevent the heart from being adversely affected. In addition, by changing the stimulation pulse intensity according to the heart rate, it is possible to effectively perform nerve stimulation regardless of variations of the depolarization intervals. In other words, with the nerve stimulation apparatus 1 of this embodiment, it is possible to effectively perform nerve stimulation without adversely affecting the heart.

Methods of deciding stimulation parameters in the respective stimulation modes (i.e., the proportional mode, the variable rate-of-change-of-intensity mode, the nonvariable mode, and the inversely proportional mode) mentioned above using the nerve stimulation apparatus 1 according to this embodiment will be described below for each stimulation mode.

<Proportional Mode>

The proportional mode is a stimulation mode in which the stimulation intensity per unit time is proportional to the heart rate.

Reduction of the heart rate, prevention of lethal arrhythmia, and a therapeutic effect on cardiac failure can be expected as results of stimulation of the vagus nerve; however, in particular, tachycardia therapy (reduction of the heart rate and prevention of lethal arrhythmia) is the aim of this stimulation mode.

Figure 5:
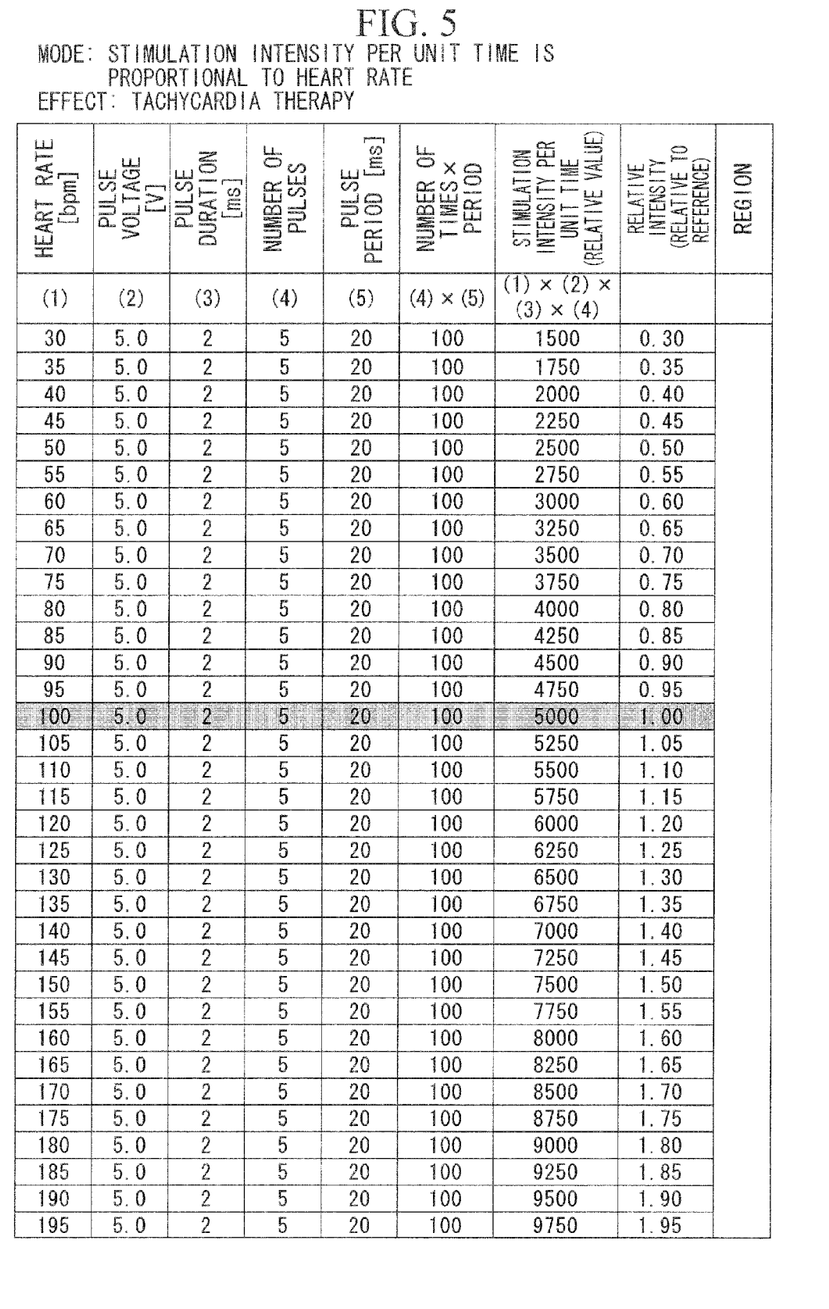
FIG. 5 is a table showing examples of parameter settings in a proportional mode.

Examples of stimulation parameters in this stimulation mode are shown in FIG. 5.

As shown in FIG. 5, in this stimulation mode, the respective stimulation parameters are set such that the stimulation intensity per unit time is proportional to the heart rate. As mentioned above, the stimulation parameters include the pulse voltage, the pulse duration, the number of pulses, and the pulse period. The stimulation intensity per unit time (relative value) is defined by the product of the heart rate, the pulse voltage, the pulse duration, and the number of pulses. In addition, the product of the number of pulses and the pulse period defines a pulse output period, and it needs to be shorter than the cardiac refractory period (in this example, 150 ms).

In FIG. 5, in the case where the stimulation intensity (5000) for the heart rate of 100 bpm (the pulse voltage: 5.0 V, the pulse duration: 2 ms, the number of pulses: five times, and the pulse period: 20 ms) is set as a reference, the relative intensity means the magnitude of the stimulation intensity for the respective heart rates relative to the reference.

As described above, when the proportional mode is set using the nerve stimulation apparatus 1 according to this embodiment, the stimulation pulses are transmitted to the vagus nerve, and the controller 5 causes the intensity of the stimulation pulses output from the stimulation-pulse output unit 4 to be changed in proportion to the heart rate obtained on the basis of the cardiac event detected by the cardiac-event detector 3.

Figure 6:
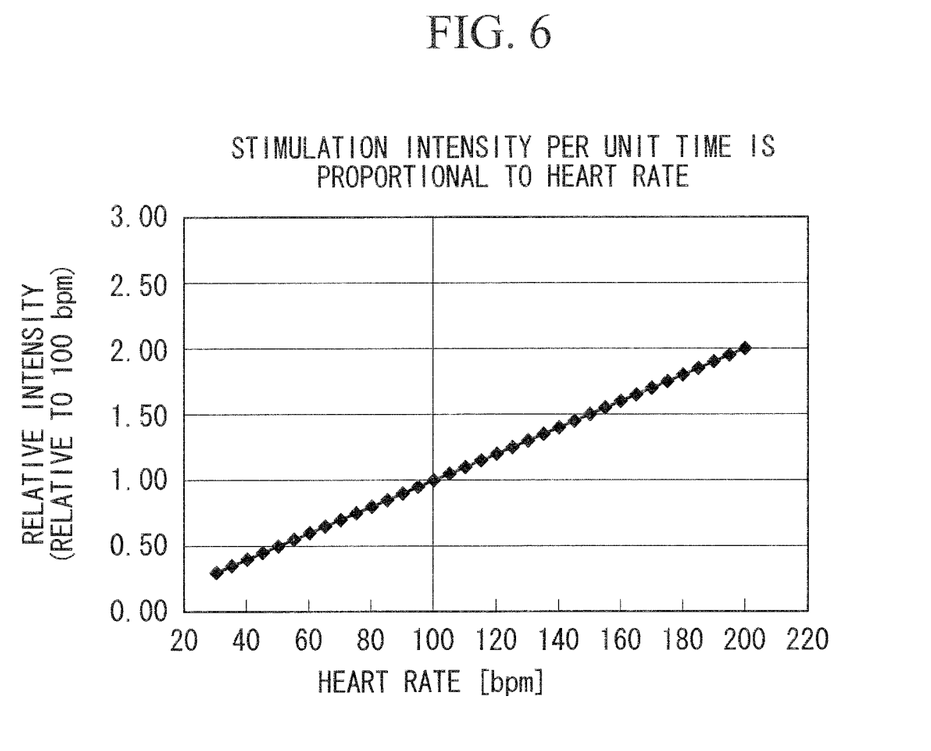
FIG. 6 is a graph showing the relationship between the heart rate and the relative intensity of stimulation pulses in the proportional mode.

By doing so, regardless of the durations of the depolarization intervals, as shown in FIG. 6, it is possible to stimulate the vagus nerve by changing the intensity of the stimulation pulse per unit time in proportion to the heart rate and to perform an effective tachycardia therapy.

<Variable Rate-of-Change-of-Intensity Mode>

The variable rate-of-change-of-intensity mode is a stimulation mode in which the rate of change of the stimulation intensity per unit time is changed according to the heart rate.

Although a simple proportional relationship is involved in the aforementioned proportional mode, the variable rate-of-change-of-intensity mode can further increase the intensity when the heart rate is high.

Figure 7:
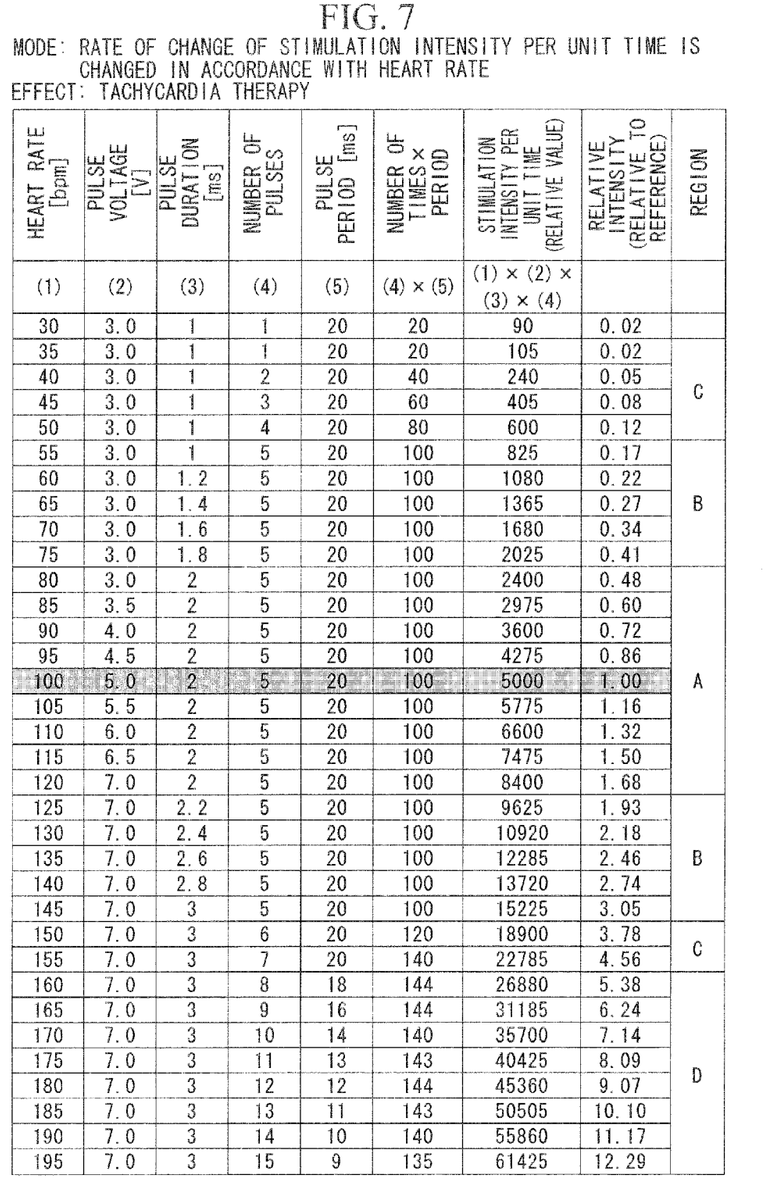
FIG. 7 is a table showing examples of parameter settings in a variable rate-of-change-of-intensity mode.

Examples of stimulation parameters in this stimulation mode are shown in FIG. 7.

As shown in FIG. 7, in this stimulation mode, the respective stimulation parameters are set such that the rate of change of the stimulation intensity per unit time is changed in accordance with the heart rate.

In this stimulation mode, the reference stimulation parameters are the same as the respective parameter values (pulse voltage: 5.0 V, pulse duration: 2 ms, number of pulses: 5, and pulse period: 20 ms) when the heart rate is 100 bpm. In addition, the amounts of change in the parameters are set as follows: pulse voltage: 0.5 V, pulse duration: 0.2 ms, number of pulses: 1, and pulse period: 1 ms.

As divisions for changing the stimulation parameters, analysis is possible by dividing the parameters into four regions A to D.

In the region A, the stimulation intensity per unit time is adjusted by changing the pulse voltage. In this example, the variable range of the pulse voltage is set from 3.0 V to 7.0 V.

In the region B, the stimulation intensity per unit time is adjusted by changing the pulse duration. In this example, the variable range of the pulse duration is set from 1 ms to 3 ms. At this time, the pulse voltage is the upper limit or the lower limit.

In the region C, the stimulation intensity per unit time is adjusted by changing the number of pulses. At this time, the pulse voltage and the pulse duration are the upper limits or the lower limits.

In the region D, the stimulation intensity per unit time is adjusted by changing the number of pulses and the pulse period. At this time, adjustment is made such that the product of the number of pulses and the pulse period does not exceed the cardiac refractory period (in this example, 150 ms).

As described above, when the variable rate-of-change-of-intensity mode is set using the nerve stimulation apparatus 1 according to this embodiment, the stimulation pulses are transmitted to the vagus nerve, and the controller 5 causes the rate of change of the intensity of the stimulation pulses output from the stimulation-pulse output unit 4 to be changed according to the heart rate obtained on the basis of the cardiac event detected by the cardiac-event detector 3.

Figure 8:
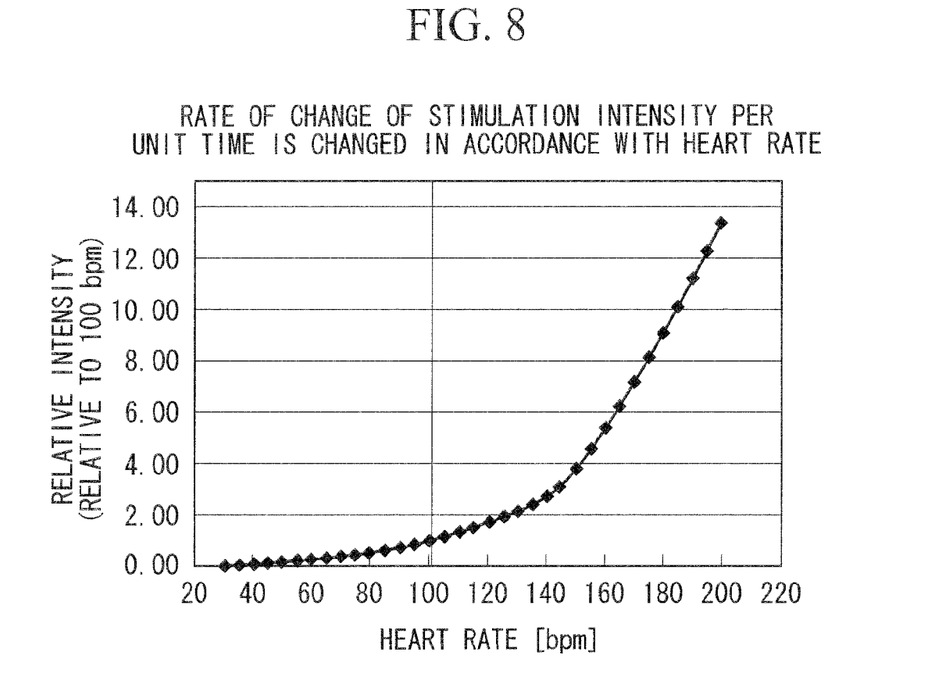
FIG. 8 is a graph showing the relationship between the heart rate and the relative intensity of stimulation pulses in the variable rate-of-change-of-intensity mode.

By doing so, regardless of the durations of the depolarization intervals, as shown in FIG. 8, it is possible to stimulate the vagus nerve by changing the rate of change of the stimulation pulse intensity according to the heart rate to change the stimulation pulse intensity, and in particular, it is possible to perform an effective tachycardia therapy when the heart rate is high.

<Nonvariable Mode>

The nonvariable mode is a mode in which the stimulation intensity per unit time is constant regardless of the heart rate.

In this stimulation mode, the aim is to treat cardiac failure with stimulation of the vagus nerve. With this stimulation mode, it is possible to constantly provide a patient with stimulation at a level decided by a doctor without being affected by fluctuation of the heartbeat.

Figure 9:
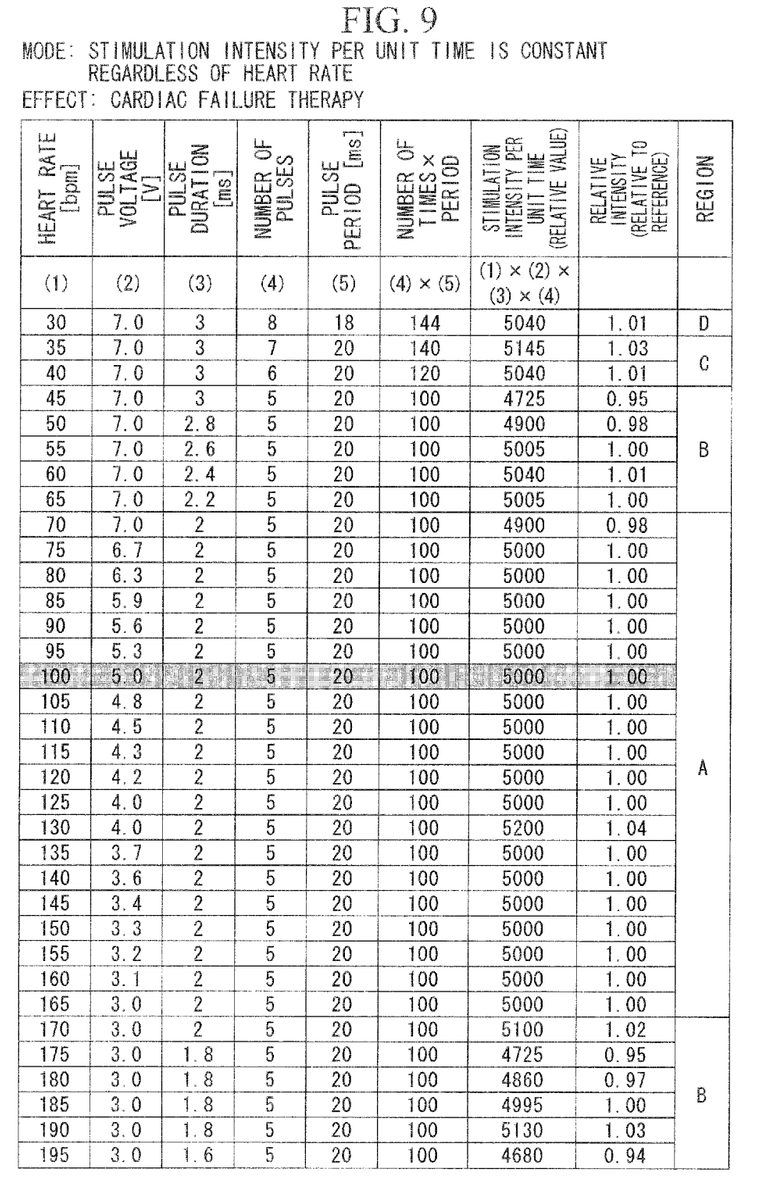
FIG. 9 is a table showing examples of parameter settings in a nonvariable mode.

Examples of stimulation parameters in this stimulation mode are shown in FIG. 9.

As shown in FIG. 9, in this stimulation mode, the respective stimulation parameters are set such that the stimulation intensity per unit time is kept constant regardless of the heart rate.

In this stimulation mode, the reference stimulation parameters are the same as the respective parameter values (pulse voltage: 5.0 V, pulse duration: 2 ms, number of pulses: 5, and pulse period: 20 ms) when the heart rate is 100 bpm. In addition, the amounts of change in parameters are set as followings: pulse voltage: 0.1 V, pulse duration: 0.2 ms, number of pulses: 1, and pulse period: 1 ms.

As divisions for changing the stimulation parameters, similarly to the variable rate-of-change-of-intensity mode (see FIG. 7), analysis is possible by dividing the parameters into four regions A to D.

In the region A, the stimulation intensity per unit time is adjusted to be constant by changing the pulse voltage. In this example, the variable range of the pulse voltage is set from 3.0 V to 7.0 V.

In the region B, the stimulation intensity per unit time is adjusted to be a constant by changing the pulse duration. In this example, the variable range of the pulse duration is set to 1 ms to 3 ms. At this time, the pulse voltage is the upper limit or the lower limit.

In the region C, the stimulation intensity per unit time is adjusted so as to become constant by changing the number of pulses. At this time, the pulse voltage and the pulse duration are the upper limits or the lower limits.

In the region D, the stimulation intensity per unit time is adjusted so as to become constant by changing the number of pulses and the pulse period. At this time, adjustment is made such that the product of the number of pulses and the pulse period do not exceed the cardiac refractory period (in this example, 150 ms).

As described above, when the nonvariable mode is set using the nerve stimulation apparatus 1 according to this embodiment, the stimulation pulses are transmitted to the vagus nerve, and the controller 5 controls the stimulation-pulse output unit 4 such that the stimulation pulse intensity becomes constant according to the heart rate obtained on the basis of the cardiac event detected by the cardiac-event detector 3.

Figure 10:
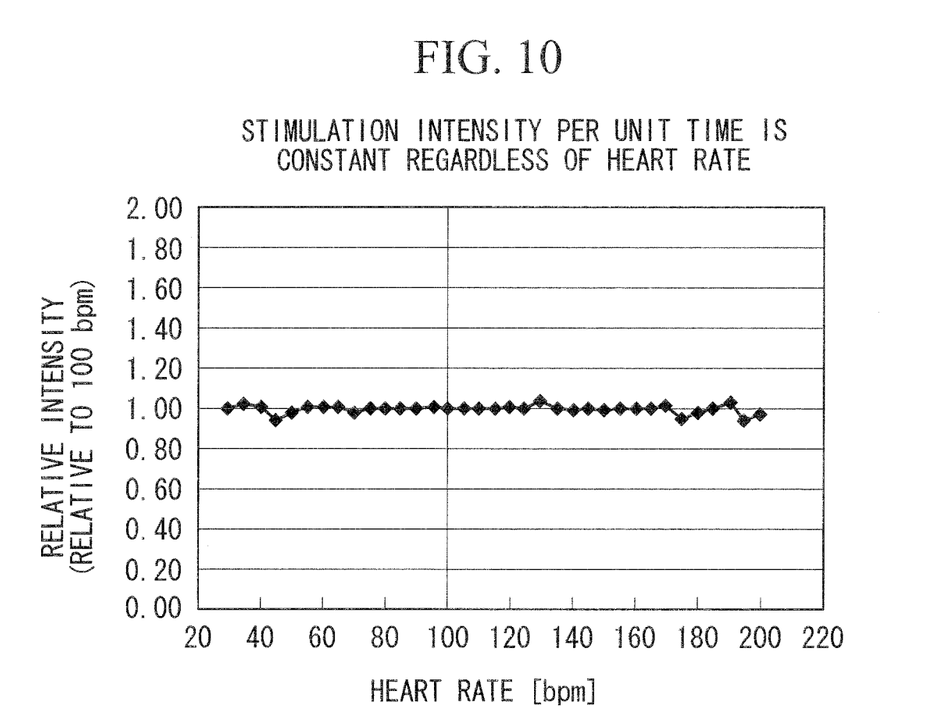
FIG. 10 is a graph showing the relationship between the heart rate and the relative intensity of stimulation pulses in the nonvariable mode.

By doing so, regardless of the duration of the depolarization intervals, as shown in FIG. 10, it is possible to stimulate the vagus nerve while keeping the stimulation pulse intensity constant and to perform effective therapy for cardiac failure.

<Inversely Proportional Mode>

The inversely proportional mode is a stimulation mode in which the stimulation intensity per unit time is inversely proportional to the heart rate.

In this stimulation mode, the heart rate can be increased by stimulating the sympathetic nerve, and therefore, this mode can be applied to bradycardia therapy.

Figure 11:
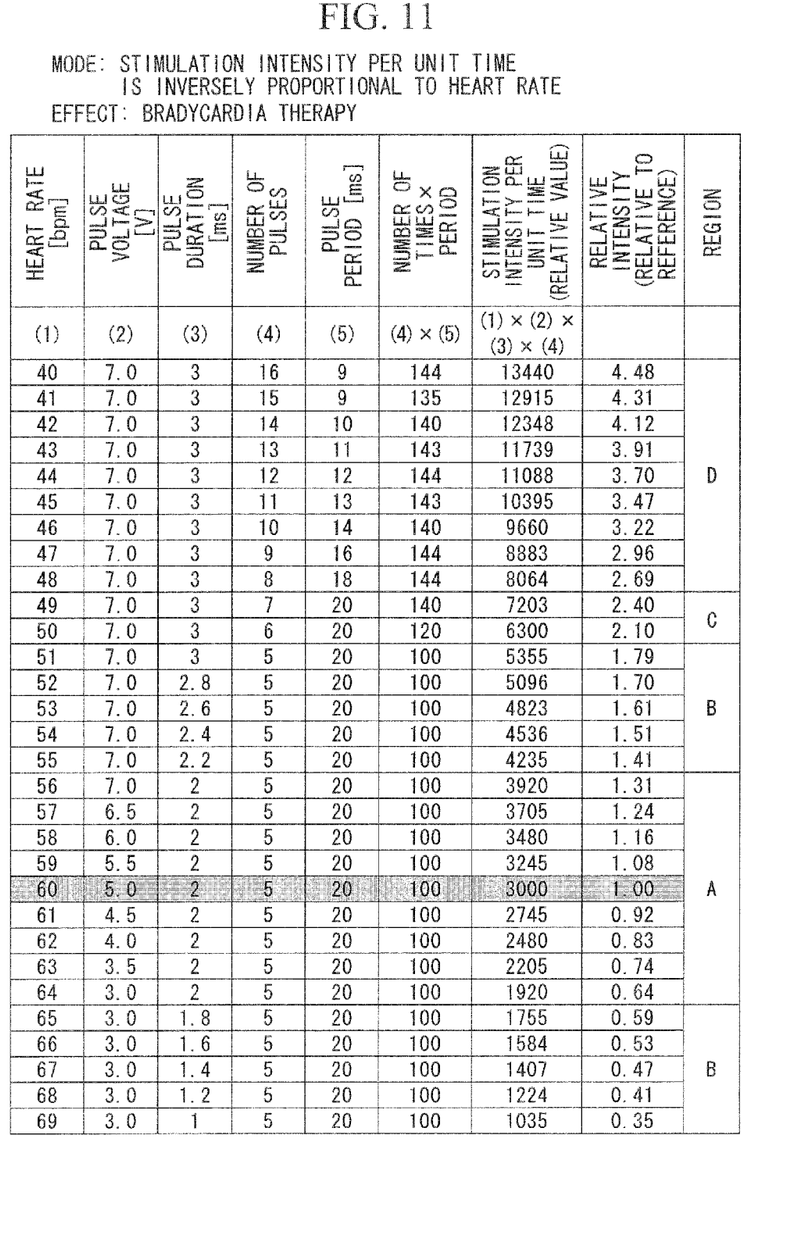
FIG. 11 is a table showing examples of parameter settings in an inversely proportional mode.

Examples of stimulation parameters in this stimulation mode are shown in FIG. 11.

As shown in FIG. 11, in this stimulation mode, the respective stimulation parameters are set such that the stimulation intensity per unit time is inversely proportional to the heart rate.

In this stimulation mode, the reference stimulation parameters are the same as the respective parameter values (pulse voltage: 5.0 V, pulse duration: 2 ms, number of pulses: 5, and pulse period: 20 ms) when the heart rate is 60 bpm. In addition, the amounts of change in parameters are set as followings: pulse voltage: 0.5 V, pulse duration: 0.2 ms, number of pulses: 1, and pulse period: 1 ms.

As divisions for changing the stimulation parameters, similarly to the variable rate-of-change-of-intensity mode (see FIG. 7), analysis is possible by dividing the parameters into four regions A to D.

In the region A, the stimulation intensity per unit time is adjusted by changing the pulse voltage. In this example, the variable range of the pulse voltage is set from 3.0 V to 7.0 V.

In the region B, the stimulation intensity per unit time is adjusted by changing the pulse duration. In this example, the variable range of the pulse duration is set to 1 ms to 3 ms. At this time, the pulse voltage is the upper limit or the lower limit.

In the region C, the stimulation intensity per unit time is adjusted by changing the number of pulses. At this time, the pulse voltage and the pulse duration are the upper limits or the lower limits.

In the region D, the stimulation intensity per unit time is adjusted by changing the number of pulses and the pulse period. At this time, adjustment is performed such that the product of the number of pulses and the pulse period does not exceed the cardiac refractory period.

As described above, when the inversely proportional mode is set using the nerve stimulation apparatus 1 according to this embodiment, the stimulation pulses are transmitted to the sympathetic nerve, and the controller 5 causes the intensity of the stimulation pulses output from the stimulation-pulse output unit 4 to be changed in inverse proportion to the heart rate obtained on the basis of the cardiac event detected by the cardiac-event detector 3.

Figure 12:
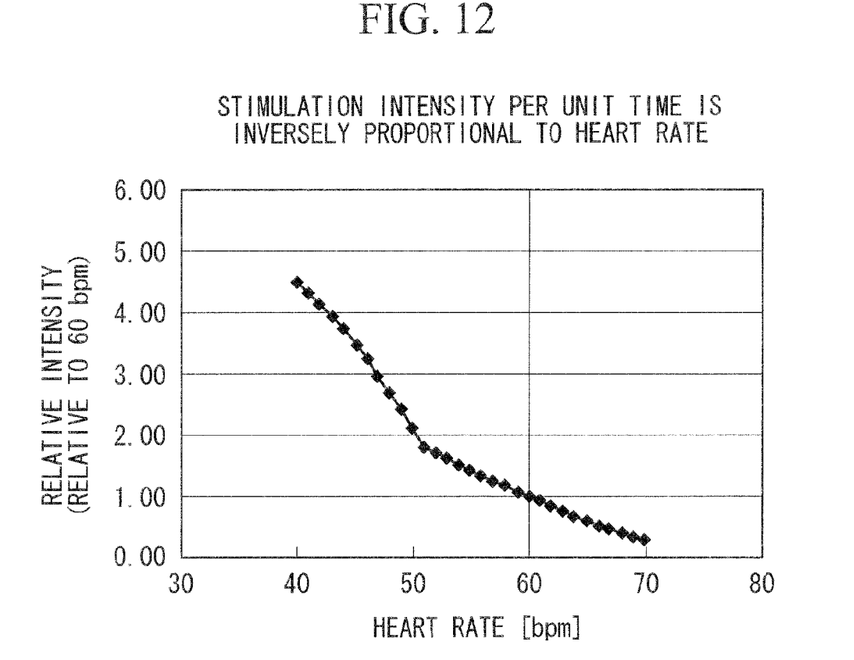
FIG. 12 is a graph showing the relationship between the heart rate and the relative intensity of stimulation pulses in the inversely proportional mode.

By doing so, regardless of the durations of the depolarization intervals, as shown in FIG. 12, it is possible to stimulate the sympathetic nerve by changing the stimulation pulse intensity in inverse proportion to the heart rate and to perform effective bradycardia therapy.

Although an embodiment of the present invention has been described above in detail with reference to the drawings, the specific configurations are not limited to this embodiment, and design alterations and the like within a range that does not depart from the spirit of the present invention are encompassed.

For example, the heart rate is exemplified by the instantaneous heart rate obtained from two depolarizations; however, the controller 5 may hold depolarization intervals for several depolarizations and calculate the average thereof. By doing so, it is possible to suppress sudden change in the stimulation parameters.

In addition, in each of the stimulation modes, all of the parameters, i.e., the pulse voltage, the pulse duration, the number of pulses, and the pulse period are changed; however, just some of the parameters may be unchanged.

In addition, in this embodiment, a predetermined value is stored in the controller 5 and the apparatus is controlled by performing determinations on the basis of the predetermined value; however, the nerve stimulation apparatus may be provided with a storage unit, and values may be stored in the storage unit.

What is claimed is:

1. A nerve stimulation apparatus comprising:
   a stimulation-signal output unit configured to output a nerve stimulation signal;
   a cardiac-event detector configured to detect a cardiac event; and
   a controller configured to control the stimulation-signal output unit so as to output, during a cardiac refractory period, the nerve stimulation signal having an intensity that corresponds to a heart rate obtained on the basis of the cardiac event detected by the cardiac-event detector;
   wherein the nerve stimulation signal is transmitted to a sympathetic nerve, and
   the controller changes an intensity of the nerve stimulation signal output from the stimulation-signal output unit in inverse proportion to the heart rate obtained on the basis of the cardiac event detected by the cardiac-event detector.

* * * * *